US008728058B2

(12) United States Patent  (10) Patent No.: US 8,728,058 B2
Schertiger  (45) Date of Patent: May 20, 2014

(54) TELESCOPIC DEVICE

(75) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/512,028

(22) PCT Filed: Nov. 25, 2010

(86) PCT No.: PCT/DK2010/050320
§ 371 (c)(1),
(2), (4) Date: May 25, 2012

(87) PCT Pub. No.: WO2011/063816
PCT Pub. Date: Jun. 3, 2011

(65) Prior Publication Data
US 2012/0271281 A1  Oct. 25, 2012

(30) Foreign Application Priority Data

Nov. 26, 2009 (DK) .................................. 2009 70231

(51) Int. Cl.
*A61M 25/00* (2006.01)
*A61M 25/01* (2006.01)
(52) U.S. Cl.
CPC ... *A61M 25/0074* (2013.01); *A61M 2025/0175* (2013.01)
USPC ....................................................... 604/544
(58) Field of Classification Search
CPC ................. A61M 25/0014; A61M 2025/0175; A61M 25/0074; A61M 25/0097; A61M 2025/0006; A61M 2025/0024
USPC ........ 604/40, 42, 48, 517, 544; 606/191–200; 623/1.11
See application file for complete search history.

(56) References Cited

U.S. PATENT DOCUMENTS

| 7,655,000 B2 * | 2/2010 | Walls et al. .................... | 604/544 |
| 2004/0158231 A1 * | 8/2004 | Tanghoj et al. ................ | 604/544 |
| 2005/0049577 A1 * | 3/2005 | Snell et al. ..................... | 604/544 |
| 2012/0179144 A1 * | 7/2012 | Carleo .......................... | 604/544 |

FOREIGN PATENT DOCUMENTS

| WO | 03002179 | 1/2003 | |
| WO | 2008138351 | 11/2008 | |
| WO | 2008138352 | 11/2008 | |
| WO | WO 2008138351 A1 * | 11/2008 | ............ A61M 25/00 |
| WO | WO 2008138352 A1 * | 11/2008 | ............ A61M 25/00 |

* cited by examiner

*Primary Examiner* — Philip R Wiest
*Assistant Examiner* — Benjamin Klein
(74) *Attorney, Agent, or Firm* — Coloplast Corp., Coloplast A/S; Nick Baumann

(57) ABSTRACT

A telescopic device comprising a first telescopic member and a second telescopic member, where the second telescopic member is displaceably arranged within the first telescopic member in a first and a second axial direction along the longitudinal axis of the first telescopic member, a coupling arrangement for limiting the displacement of the second telescopic member relative to the first telescopic member where the coupling arrangement has a first and a second coupling configuration.

24 Claims, 3 Drawing Sheets

TELESCOPIC DEVICE

FIELD OF THE INVENTION

The present invention relates to a telescopic device and a coupling arrangement for a telescopic device. In particular, the invention relates to a telescopic catheter and more particularly to a telescopic urinary intermittent catheter or a telescopic urinary intermittent catheter package.

BACKGROUND OF THE INVENTION

Urinary catheters are used as a tool assisting in the draining of the urinary bladder of persons with reduced or non-existing bladder control. The reduced or non-existing bladder control may either be temporary or permanent, where a temporary loss of bladder control may be caused by trauma, loss of consciousness or illness, as an example. An example of a permanent loss of bladder control may be where a loss of a neural connection between the brain or spinal cord and the urinary bladder occurs due to a trauma to the spinal cord, as is often the case with para- and/or tetraplegics.

One example of a urinary catheter which is widely used for draining urine from the urinary bladder is where a catheter tube is inserted into the urethra of a user and the tip of the catheter tube is maneuvered into the urinary bladder forcing the urethral sphincter open and thus providing a drainage channel from the urinary bladder and out of the body via the catheter tube. There are two types of catheters which are commonly used: the permanent catheter and the intermittent catheter. The permanent catheter is a highly flexible catheter which is inserted into the body by medical professionals and stays there for a long period at a time, and the catheter is anchored inside the bladder. The intermittent catheter is usually a single use catheter or a multiple use catheter, which is inserted into the urethra/bladder by the user for immediate drainage of their urinary bladder and is removed from the urethra/bladder subsequent to the drainage. The following disclosure will primarily be concentrated on the intermittent urinary catheter.

There are a number of different types of intermittent catheters which are currently available for the user, such as the SpeediCath™ and EasiCath™ marketed by Coloplast A/S which are conventional one-piece catheter tubes which have an outlet at the distal end which may be used to connect the catheter to a urinary bag for collecting the urine drained from the urine bladder.

Another type of a catheter is disclosed in WO 03/002179 which is a telescopic catheter where one of the telescopic elements is the catheter package and another telescopic element is the catheter member that telescopes from the catheter package. The telescopic catheter is collapsed during storage and transport and extended for insertion into the urethra, providing female users with a compact and discrete catheter which may be used anywhere and without any significant preparation time.

Another type of catheter is disclosed in WO 2008/138351 which discloses a telescopic device having a first tubular member and an extension member having a coupling member that limits the displacement of the extension member within the first tubular member, where the coupling member engages the interior of the first tubular member. This device is a telescopic intermittent catheter, which is also adapted for use by a male user, where the first tubular member and the extension member are adapted in such a way that both telescopic members are adapted to be inserted into the urethra of the user.

The telescopic catheters known in the art, as discussed above, are locked in their extended state, so that the extension member or the telescopic element is prevented from collapsing into their compacted state. This means that after use it is difficult to dispose of the catheter in a discrete manner, for example by dropping it into a garbage bin or back into a storage area, such as a handbag or a pocket.

Thus, there is a need for a telescopic device that may be extended from a collapsed state to an extended state and optionally may subsequently be collapsed into a collapsed state.

SUMMARY OF THE INVENTION

According to the invention there is provided a telescopic device comprising a first telescopic member and a second telescopic member, where the second telescopic member is displaceably arranged within the first telescopic member so that the second telescopic member can be moved in a first and a second axial direction along the longitudinal axis of the first telescopic member, a coupling arrangement for limiting the displacement of the second telescopic member relative to the first telescopic member where the coupling arrangement has a first and a second coupling configuration, where the first coupling configuration limits the displacement in the first axial direction allowing displacement in the opposite second axial direction, and the second coupling configuration limits the displacement in the second axial direction allowing displacement in the opposite first axial direction, where the coupling arrangement is adapted to convert from the first coupling configuration to the second coupling configuration, and vice versa by an application of force above a predetermined level to the second telescopic member in the axial direction, which displacement is limited in the first or second coupling configuration.

This means that the first and second telescopic members may be maneuvered relative to each other in one direction at any given time, provided that the telescopic device is not fully extended, and where the coupling arrangement prevents the first and second telescopic members from being maneuvered in the opposite direction. As an example, if the coupling arrangement allows the second telescopic member to be pulled or pushed in a direction away from the first telescopic member, the coupling arrangement prevents any movement of the second telescopic member in the opposite direction, i.e. to be pushed into the first telescopic member. Thus, in the case where the telescopic device is a urinary catheter, this arrangement allows the telescopic device to be arranged in an extended state, for insertion of the catheter into the urinary channel, and during the insertion the telescopic urinary catheter will be maintained in its extended state without being collapsed or reduced in length.

Furthermore, after use the user may apply a force above a predetermined level to the second telescopic member, and thus converting the coupling arrangement into a second coupling configuration, where the telescopic urinary catheter may be collapsed for a discrete disposal or a discrete storage, where the urinary catheter is prevented from extending to a length that is longer than the collapsed length, This means, that after disposal or storage after use, the risk that the catheter will extend from its collapsed state is reduced considerably.

However, should the user wish to extend the catheter from its collapsed state to its extended state, the user can apply a force above a predetermined level to the second telescopic member, and the coupling arrangement will convert from its second coupling configuration to its first coupling configuration, allowing the second telescopic member to be extended from the first telescopic member, as discussed earlier. This may be advantageous, if the telescopic urinary catheter is of a kind that may be reused. Thus, the catheter may be extended for catheterization and collapsed for storage more than one time.

Another advantage of the present disclosure is obtained during the insertion of a catheter into the human or animal urethra. In case of a blockage or constriction in the urethra during the insertion or if the urinary sphincter of the urine bladder is for some reason unusually tight, the present arrangement minimizes the risk of the catheter causing trauma to the urethra or the urinary sphincter. The reason for this is that the second telescopic member may be prevented from maneuvering inside the urethra or into the urine bladder and the force applied to insert the urinary catheter would be transferred to the second telescopic member by the blockage or constriction, and if the insertion force exceeds the predetermined level the coupling arrangement may convert from the first coupling configuration to the second coupling configuration. This conversion affects the telescopic urinary catheter in such a way that the telescopic urinary catheter may be prevented from being maneuvered further into the urethra or the urinary bladder and thus the user would not risk damaging or traumatizing the urethra, the urinary sphincter or the urine bladder by the increased force that would otherwise be necessary to insert the catheter into the urinary bladder. Thus, the coupling arrangement provides a means for reducing the risk of damaging or traumatizing the urethra, urinary sphincter or the urine bladder in case of blockages or constrictions during the insertion.

In one embodiment of the present invention, the application of force to the second telescopic member may be provided by pushing the second telescopic member in a direction towards the first telescopic member. The application of force to the second telescopic member may be transmitted to the coupling arrangement, while the coupling arrangement is preventing the second telescopic member from being displaced in a direction into or out of the first telescopic member. Thus, the transmitted force applied to the coupling arrangement by the application of pushing force to the second telescopic member may cause the coupling arrangement to convert from the first coupling configuration to the second coupling configuration, or vice versa. The pushing force may be applied by an application of force to the free end of the second telescopic member, or by applying pressure to the outer surface of the second telescopic member and applying force in the required direction. According to the teachings of the present disclosure, alternative methods of applying force to the second telescopic member may be obvious to the skilled person.

In one embodiment of the present invention, the application of force to the second telescopic member may be provided by pulling the second telescopic member in a direction away from the first telescopic member. The application of force to the second telescopic member may be transmitted to the coupling arrangement while the coupling arrangement is preventing the second telescopic member from being displaced in a direction into or out of the first telescopic member. Thus, the transmitted force applied to the coupling arrangement by the application of pulling force to the second telescopic member may cause the coupling arrangement to convert from the second coupling configuration to the first coupling configuration, or vice versa. The user may apply a pulling force to the second telescopic member by applying pressure to the outer surface of the second telescopic member, e.g. using the fingers of the hand directly or indirectly using a non-touch applicator, and pulling the second telescopic member in a direction out of the first telescopic member, or by the application of pulling force in the opposite direction, in a direction towards the first telescopic member.

A non-touch applicator may be arranged on the outer surface of the first and/or the second telescopic member allowing the user to apply pressure to the external surface of the telescopic device for the purpose of maneuvering the second telescopic member in relation to the first telescopic member without contaminating the outer surface of the first and/or the second telescopic member. The contamination of the outer surface of a telescopic device, such as a urinary catheter, may increase the risk of the user attracting a urinary tract infection, which is a common ailment for the users of intermittent urinary catheters. Another advantage of using a non-touch applicator may be that the user is prevented from getting his/her fingers soiled when maneuvering or touching a urinary catheter provided with a wetted hydrophilic surface coating or provided with a lubricating gel on the outer surface of the catheter.

In one embodiment of the present invention, the predetermined level of force may be in the range of 1-30N. The force requirements for the conversion of the coupling arrangement from the first coupling configuration to the second configuration may vary, depending on which use the telescopic device is adapted to. Thus, if the developers of a telescopic device according to this disclosure adapt the use of the telescopic device to be inserted into a highly fragile passage, the device may be adapted to convert without a significant amount of force, such as 1N in order to prevent the device from causing damage to the passage. In another example, where the telescopic device is adapted to be sturdy and has to be used to poke an object for moving or displacing the object, the force may be increased to approximately 30N, allowing a significant amount of force to be applied before the coupling arrangement converts. On the basis of the current disclosure, it would be obvious to the skilled person to choose a force level that may exceed 30N, such as 60N or 100N, if the application of the telescopic device requires such a force.

In one embodiment of the present invention, the predetermined level of force may be in the range of 3-20N. The lower limit of this range, 3N, may be used when the telescopic device is a urinary or a medical catheter having a very small diameter. An example of such a telescopic device may be a urinary catheter adapted to be used in infants, where the urethra and the urinary sphincter have a small diameter and where it is important to prevent any damage to the bodily tissue of the infant. An example of a medical catheter having a relatively small diameter may be an arterial or venous catheter, where it is important that the force applied to the catheter is not so high that the catheter might inadvertently push through an arterial or venous wall. The higher limit in the range 20N may, for example, be used for a human or animal urinary catheter where the diameter of the catheter is of a large size, such as a urinary catheter for a horse, and where the walls of the urinary channel are strong enough to endure such a high force.

In another embodiment of the present invention, the predetermined level of force may be in the range of 5-15N. The lower limit of this range may be used when the telescopic device is a urinary catheter having a small diameter, such as a urinary catheter adapted to be used in children. The higher limit of this range may be used when the telescopic device is adapted for the use as a urinary catheter for full grown adults. The same considerations as mentioned in the previous paragraphs apply to this range.

In another embodiment of the present invention, the predetermined level of force may be in the range of 6-12N. The lower limit of this range may be used when the telescopic device is a urinary catheter having a medium diameter, such as a urinary catheter adapted to be used in teenagers. The higher limit of this range may be used when the telescopic device is adapted for the use as a urinary catheter for adults. The same considerations as mentioned in the previous paragraphs apply to this range.

In another embodiment of the present invention, the predetermined level of force may be in the range 8-10N. This range may be defined as the optimum range for the maximum level of force required to insert a conventional urinary catheter into a normally grown adult human. Should the force required to insert the urinary catheter exceed 10N, there is an increased risk that the urinary catheter may damage the urinary channel or the urinary sphincter, as the biological tissue in the urinary system is vulnerable. In this embodiment, should the level of force applied to the telescopic device exceed approximately 10N, the coupling arrangement may convert, and the user may not be able to insert the urinary catheter further up into the urinary channel and the risk of damaging the biological tissue is reduced significantly. However, should the force level be set at a level that is smaller than approximately 8N, a normally skilled user of a urinary catheter might have trouble inserting the catheter without making the coupling arrangement convert. However, as mentioned earlier, specific circumstances might require the level of force to be higher or lower, depending on the future development of lubricants or low-friction surfaces of urinary catheters, development of the shape and size of the catheter, etc. Based on the teachings of the present disclosure, it is obvious to the skilled person that improvements and changes in the design of a urinary catheter might lead to a predetermined level of force in a different range than the optimum range.

Another factor that might influence the choice of ranges for the predetermined force may be a factor such as the hand dexterity of the user and possibly the level of paralysis in para- or tetraplegic users.

In one embodiment of the present invention, the coupling arrangement may be adapted to convert by maneuvering the second telescopic member relative to the first telescopic member in a direction that is opposite to the direction allowing displacement in the first or the second coupling configuration. In a situation where the coupling arrangement prevents the telescopic device from being collapsed, the second telescopic member may be maneuvered in such a way that the user attempts to collapse the catheter. This causes the coupling arrangement to convert, and the telescopic device may be prevented from being extended. Similarly, if the telescopic device is arranged in such a way that it is prevented from being extended, the second telescopic member may be maneuvered in such a way that the user attempts to extend the catheter, causing the coupling arrangement to convert and the telescopic device is back in a situation where the device is prevented from being collapsed.

In one embodiment of the present invention, the coupling arrangement may comprise a coupling member having a proximal end and a distal end and a coupling ring encircling an outer surface of the coupling member, where the outer surface of the coupling member may be provided with a central part having a first outer diameter, a first tapered surface proximal to the first central area terminating in a second outer diameter that is smaller than the first outer diameter and a second tapered surface distal to the central area terminating in a third outer diameter that is smaller than the first outer diameter. The coupling ring may be adapted to be maneuverable along a longitudinal axis of the coupling member, so that it may be moved from the proximal end of the coupling member to the opposite proximal end, and vice versa. The coupling ring may be a flexible ring made of a resilient elastic or non-elastic material having a material memory, so that when no stress or strain is applied to the coupling ring it has a natural diameter, but when stress or strain is applied to it, it is capable of expanding to a larger diameter.

Thus, when the ring is maneuvered from the distal end of the coupling member to the central area of the coupling member, the diameter of the ring increases during the ascend up the tapered surface distal to the central part, and when the ring is moved from the central area towards the proximal end, the diameter of the ring decreases during the descend down the tapered surface proximal to the central area. The ring may also be maneuvered in the opposite direction, where the diameter of the coupling ring expands and contracts in the same manner.

In one embodiment of the present invention, the coupling member may be attached to a distal end of the second telescopic member.

In one embodiment of the present invention, the coupling ring may engage an inner surface of the first telescopic member.

In the event where the coupling member is inside the first telescopic member, having an inner diameter that is equal to or larger than the first outer diameter of the central area of the coupling member, the coupling ring may engage the inner surface of the first telescopic member, and the inner surface of the first telescopic member may prevent the coupling ring from being maneuvered to the central area, thus preventing the movement of the coupling member in one longitudinal direction. However, should the coupling member, the coupling ring or the inner surface of the first telescopic member be provided as a resilient, compressible and/or extendable material, or a combination of resilience between the items, an increased stress or strain to the coupling member may allow the coupling member to ascend to the central area and over to the opposite tapered surface area, thus converting from one coupling configuration to another. The increased stress or strain may be provided as a force applied to the second coupling member.

In one embodiment of the present invention, the coupling ring may have an outer surface provided with a radial protrusion. The radial protrusion on the outer surface of the coupling ring may increase the friction between the inner surface of the first telescopic member and the coupling ring, if for example the inner surface of the first telescopic member is made of a resilient material, and during the expansion of the coupling ring, the protrusion may dig into the inner surface of the first telescopic member.

In one embodiment of a telescopic device according to the present invention, the coupling arrangement may be adapted to allow the conversion of the coupling arrangement from the first coupling configuration to the second coupling configuration but prevent the coupling arrangement from converting back to the first coupling configuration. This may be advantageous in a situation where the telescopic device is a single use intermittent urinary catheter and a user has failed in his attempt to insert the urinary catheter into the urinary channel, and the coupling arrangement of the telescopic device is converted from one coupling configuration to the other. Thus, in order to prevent the reuse of the catheter, which may cause a urinary tract infection due to a contamination on the surface of the urinary catheter, the user may only be allowed to collapse the catheter, and the conversion to the other coupling configuration is prevented. Thus, the user may not be capable of using the catheter a second time, thus minimizing the risk of a urinary tract infection. In one embodiment of the present invention, this may be achieved by providing the proximal tapered surface with a stopping means for preventing the coupling ring from maneuvering from the proximal tapered surface to the central area. The stopping means may be in the form of a ridge or a protrusion which the coupling ring cannot pass.

In one embodiment of the present invention, the telescopic device may be a urinary catheter.

In one embodiment of the present invention, the surface of the first and/or the second telescopic element may be coated with a hydrophilic coating for provision of a low friction surface.[The telescopic device may be arranged in such a way that the first telescopic member comprises a package for enclosing the second telescopic member, and the second telescopic member may be provided with a hydrophilic coating, whereas the first telescopic member is non-coated, so that the telescopic device may be maneuvered while holding the first telescopic member. In the event where the first telescopic member and the second telescopic members are both adapted to enter into the urinary channel, both telescopic members may be provided with a hydrophilic coating.

In one embodiment of the present invention, the first and the second telescopic members may be uncoated.

In one embodiment of the present invention, the telescopic device may be packed for storage and/or transport with a liquid swelling medium for wetting the hydrophilic coating and for maintaining the hydrophilic coating in a fully hydrated state during storage and/or transport. By the arrangement of a liquid swelling medium maintaining the hydrophilic coating in a fully hydrated state during storage and/or transport, the user may be provided with a ready to use catheter that may be used directly after removing the telescopic device from its package. Furthermore, the user is not required to bring any accessories, such as lubricating gel or an external source of liquid swelling medium for the preparation of the catheter.

In one embodiment of the present invention, the second telescopic member may be a catheter tube having a wall defining an inner lumen, where the wall is provided with drainage eyes and a proximal end having an insertable tip, closing off the inner lumen of the catheter tube. The telescopic device may therefore be used as a urinary catheter, where the second telescopic member is adapted to be inserted into the urinary channel and where the insertable tip is adapted to penetrate the urinary sphincter, so that the catheter tube may be inserted into the urine bladder. The drainage eyes provide a liquid communication channel between the external surface of the catheter tube and the inner lumen of the catheter tube, allowing the urine to enter the drainage eyes and thus draining the urine through the inner lumen of the catheter tube. The first telescopic member may also be provided with an inner lumen, so that the first telescopic member may either function as an extension of the catheter tube in the form of a drainage hose and/or function as a second insertable catheter tube that may also be inserted into the urinary channel as an insertable extension to the second telescopic member.

In one embodiment of the present invention, the length of the first telescopic member may be equal to or larger than the length of the second telescopic member. This means that the first telescopic member may completely enclose the second telescopic member, and the first telescopic member may function as a catheter package protecting the second telescopic member from contamination from the environment during transport or storage. Furthermore, the first telescopic member may also enclose further elements that may be necessary for the urinary catheter to be in a ready to use condition, such as a liquid swelling medium providing hydration for a hydrophilic surface coating, a lubricating gel for lubricating the catheter surface, a non-touch applicator for allowing the user to handle the insertable part of the catheter without contaminating the insertable part, etc.

In one embodiment of the present invention, the first telescopic member may be a tubular element that may have walls of gas impermeable material. If the first telescopic member functions as a package for the second telescopic member, and a liquid swelling medium is provided inside the package, it may be advantageous for the package to be made of a gas impermeable material, so that any diffusion of the liquid swelling medium may be reduced or prevented and the catheter may be maintained in a wetted condition for a significant time period. A significant time period may for example be the shelf-life of the telescopic device, which may be a period of approximately 6 months to approximately 5 years.

In one embodiment of the present invention, the telescopic device may be provided in a collapsed configuration for storage or transport, where the first telescopic member encloses the second elongated member and the free ends of the first telescopic member are closed by a gas impermeable closure. This means that the first telescopic member may constitute the packaging for the second telescopic member, and thus the package as a whole may be seen as gas impermeable, so that any diffusion of the liquid swelling medium is prevented during storage or transport.

In one embodiment of the present invention, the first telescopic member may be a corrugated tubular element where the side wall may comprise alternating ridges and grooves. The alternating ridges and grooves may increase the flexibility of the side wall of the corrugated tubular element, compared with a tubular element not having alternating ridges and grooves. In order to provide the first telescopic member with a wall of flexible material, it may be provided as a side wall having alternating ridges and grooves in a radial direction of the central longitudinal axis of the first telescopic member. This means that the thickness of the material may be increased in order to provide a more gas impermeable side wall, without having to compromise significantly on the flexibility of the first telescopic member.

In one embodiment of the present invention, the first telescopic member may define a handle allowing the manipulation of the second telescopic member, This means that the first telescopic member is made of a material that is rigid enough to allow the gripping of the material during the insertion, use, removal and manipulation of the telescopic device, without deforming the material to such an extent that the first telescopic member becomes difficult to grip and/or to prevent that the walls of the first telescopic member collapse and prevent liquid flow communication through an inner lumen of the first telescopic member under the application of the gripping pressure to the side walls of the first telescopic member.

BRIEF DESCRIPTION OF THE DRAWINGS

The invention will be explained in greater detail below, describing in example and referring to further advantages of the invention with reference to the drawing, in which.

DETAILED DESCRIPTION OF THE DRAWINGS

Figure 1:
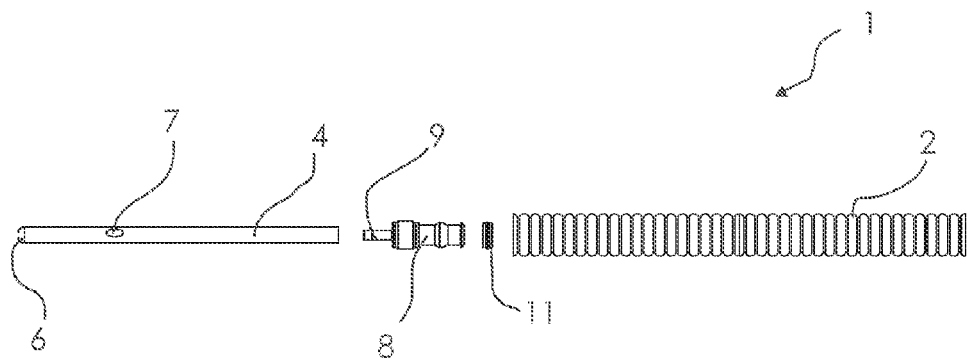
FIG. 1 shows an exploded side view of a telescopic device in accordance with the present invention.
Figure 2:
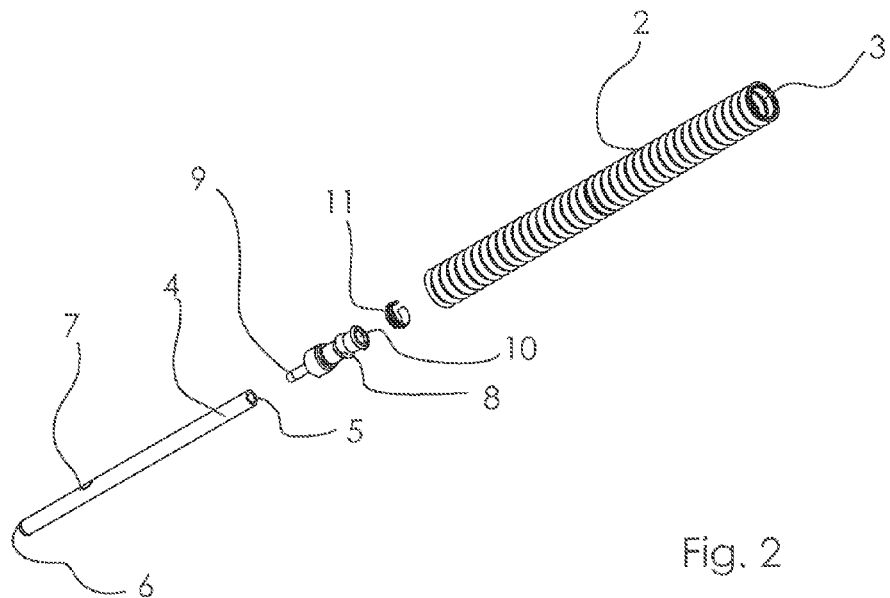
FIG. 2 shows an exploded perspective view of the same.

FIG. 1 and FIG. 2 show a telescopic device 1 in accordance with the present invention, where the telescopic device 1 is a urinary catheter kit. The urinary catheter kit 1 comprises a first telescopic member 2, which may be a corrugated tubular member having an inner lumen 3 and having walls of gas impermeable material. The side walls of the first telescopic member may be made of a material that is flexible or rigid, and the flexibility of the side walls may be altered or amended by varying the design of the alternating ridges and grooves of the corrugated material. The second catheter section 4 is a catheter tube having an inner lumen 5 along the longitudinal axis of the catheter tube 4, as is well known in the art. The catheter tube 4 is provided with an insertable catheter tip 6 which closes off the inner lumen 5 of the catheter tube at the proximal end of the catheter tube 4. In order to provide a liquid communication from the external surface of the catheter tube 4 to into the inner lumen 5, the catheter tube 4 is provided with at least one drainage eye 7, which is a through-going opening in the side wall of the catheter tube 4.

The first telescopic member 2 and the second telescopic member 4 may be assembled in a telescopic configuration, where the second telescopic member 4 projects into the inner lumen 3 of the first telescopic member 2. A coupling member 8 is provided at a distal end of the second telescopic member 4 and may be permanently attached to the inner lumen 5 of the second telescopic member using a connector 9 that may be welded, glued, shrink fitted, etc. to the inner surface of the second telescopic member 4. The assembled coupling member 8 and the second telescopic member are inserted into the inner lumen 3 of the second telescopic member, where the external surface of the coupling member has a maximal outer diameter that is equal to or smaller than the smallest inner diameter of the first telescopic member 2. The coupling member 8 has an inner lumen 10 extending along the longitudinal axis of the coupling member 8. The lumen 10 provides liquid communication between the inner lumen 5 of the second telescopic member 4 and the inner lumen 3 of the first telescopic member 2. In order to fix or restrain the first telescopic member 2 in relation to the second telescopic member 4 and the coupling means 8, a C shaped coupling ring 11 is arranged to encircle the external surface of the coupling member 8, which is shown in more detail in FIGS. 3 and 4.

Figure 3:
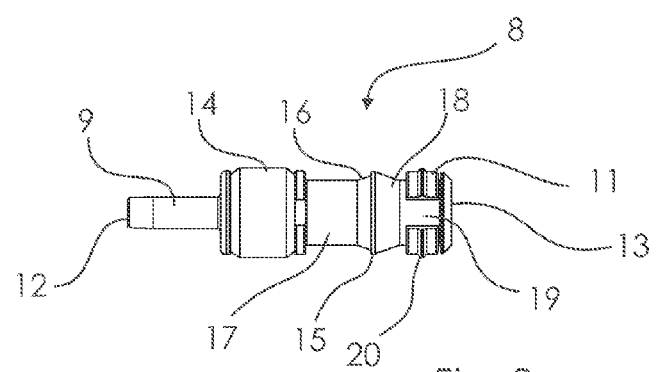
FIG. 3 shows a side view of a coupling member for use in a telescopic device in accordance with the present invention.

FIG. 3 is a side view of a coupling member 8 as shown in FIGS. 1 and 2, where the coupling ring 11 is arranged to encircle the external surface of the coupling member 8. The coupling member 8 has a proximal end 12 and a distal end 13, where the proximal end 12 is provided with a connector 9 that connects to the second telescopic member (see FIG. 1). The coupling member 8 has a sealing member 14 that encircles the entire external surface of the coupling member 8, and it may be of a flexible and/or resilient material such as rubber, plastic, etc. The external diameter of the sealing member 14 is approximately equal to the inner diameter of the first telescopic member (2 in FIG. 1), so that the sealing member prevents any liquid communication past the coupling member 8 when it is arranged inside the inner lumen of the first telescopic member.

The coupling member 8 has a central cross sectional area 15 that has a first outer diameter, and a first tapered surface 16 that is proximal to the central cross sectional area 15 which terminates in a first surface area 17 having a second outer diameter that is smaller than the first outer diameter of the central cross sectional area 15. The coupling member 8 is further provided with a second tapered surface 18 that is distal to the central cross sectional area 15, which terminates in a second surface area 19 having a third outer diameter that is smaller than the first outer diameter of the central cross sectional area 15. The coupling ring 11 encircles the outer surface of the coupling member 8 and may be moved from the distal end 13 of the coupling member 8 in a direction towards the proximal end 12 of the coupling member 8. The cross sectional area of the inner surface of the coupling ring 11 has a diameter that is equal to or larger than the outer diameter of the first 17 or the second surface area 19, in such a way that the coupling member is not restricted from movement along the surface area of the coupling member.

Figure 4A:
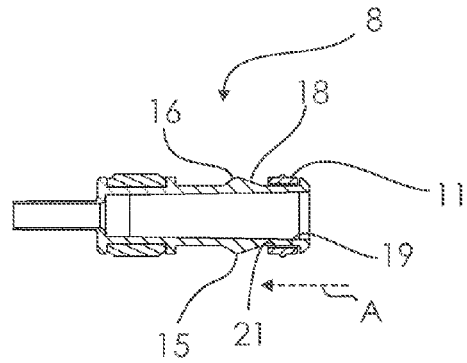
FIG. 4a-c show a side sectional view of a coupling member in a first coupling configuration, a second coupling configuration and a second coupling configuration according to one embodiment of the present invention, respectively.
Figure 4B:
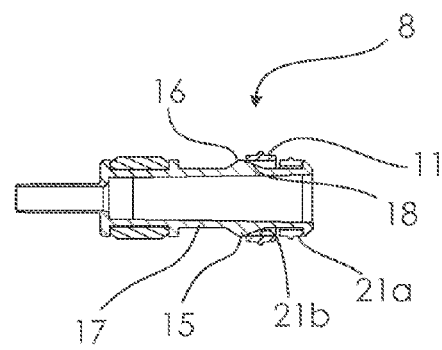

FIG. 4a shows a side sectional view of the coupling i ember 8 having a coupling ring 11 of a non-resilient material encircling the second surface area 19. If the coupling ring 11 is pushed or pulled in the direction A, the inner surface 20, as shown in FIG. 3, of the coupling ring 11 abuts the distal tapered surface 18, and the increase in diameter of the tapered surface 18 causes the coupling ring to expand and the diameter of the inner surface 20 expands causing the outer diameter of the coupling ring 11 to increase accordingly into a configuration as shown in FIG. 4b. In FIG. 4b the coupling ring 11 is arranged on the distal tapered surface 18, close to the central area 15, where the inner and/or the outer diameter 21b of the coupling ring in this position has increased from its starting position 21a. if the coupling ring 11 is pushed or pulled further in a proximal direction, the coupling ring 11 will expand and pass the central area 15 and descend via the proximal tapered surface 16 onto the first surface area 17, where the coupling ring has returned to its original non-expanded diameter.

Figure 4C:
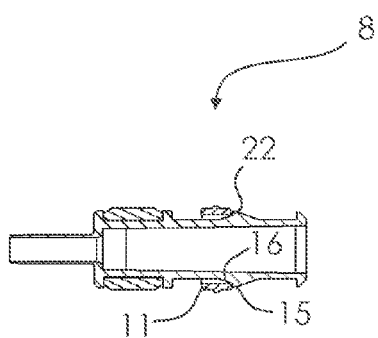

FIG. 4c shows an alternative embodiment of the coupling member 8, where the transition between the central area 15 and the proximal tapered surface 17 is provided with a ridge 22 that prevents the coupling ring 11 from being moved from the proximal side of the central area 15 and up to the central area 15.

Figure 5A:
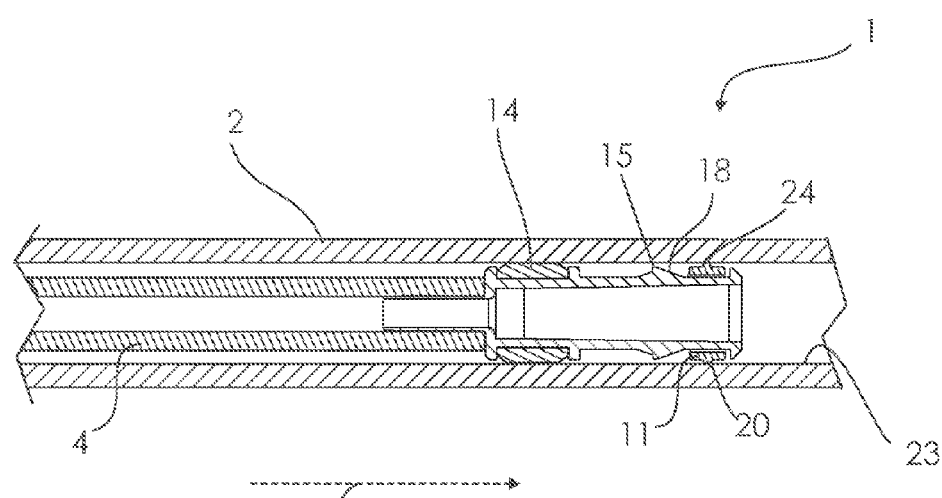
FIG. 5a shows a sectional side view of a telescopic device according to the present invention, where the coupling arrangement is in a first coupling configuration during extension.
Figure 5B:
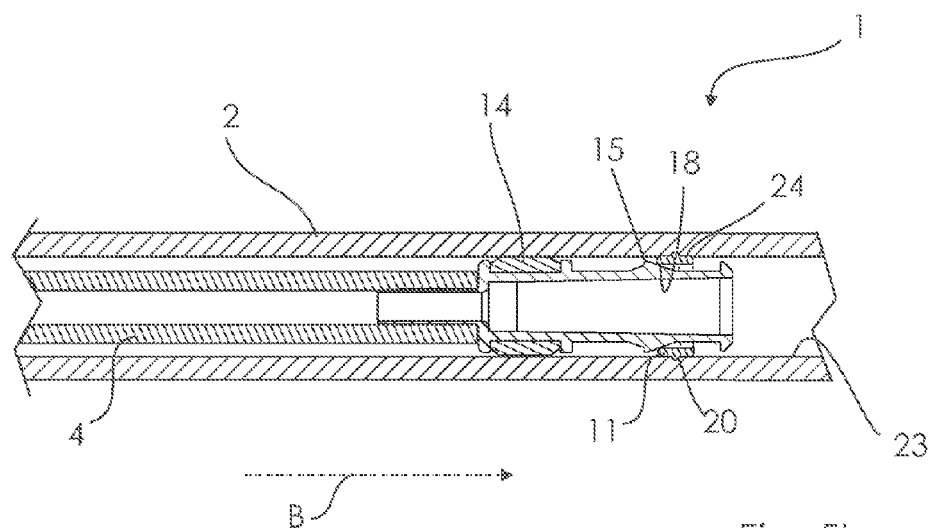
FIG. 5b shows a sectional side view of the same, where the coupling arrangement prevents the collapse of the telescopic device.

FIG. 5a shows a side sectional view of a telescopic device 1 having a first telescopic part 2 and a second telescopic part 4 inside the first telescopic part 2. The second telescopic part 4 is provided with a coupling member 8 having a sealing member 14 which has an outer diameter that is equal to or larger than the diameter of the inner surface 23 of the first telescopic member. The coupling member 8 is further provided with a coupling ring 11 having a protrusion 20, where the outer diameter of the coupling ring or the protrusion is equal to or larger than the inner diameter of the inner surface 23 of the first telescopic member 2. This means that the outer surface and/or the protrusion 20 of the coupling ring 11 is in contact with the inner surface 23 of the first telescopic member so that there are frictional forces between the two surfaces in the area 24 where there is contact. Thus, if the second telescopic member 4 is moved, pushed or pulled in a longitudinal direction shown by B, the frictional area 24 between the coupling ring 11 and the inner surface 23 ensures that the coupling ring 11 does not move relative to the first telescopic member 2. However, the coupling member 8 is moved relative to the coupling ring 11, which means that the distal tapered surface 18 is pushed into the coupling ring 11, causing the coupling ring 11 to expand and increasing the friction between the inner surface 23 of the first telescopic member 2 and the coupling ring 11, as seen in FIG. 5b. Thus, this cooperation between the coupling member, the coupling ring and the first telescopic member prevents the second telescopic member 4 from being pushed in the direction B where the force applied to the second telescopic member 4 is lower than a threshold value of force, as discussed earlier.

Figure 5C:
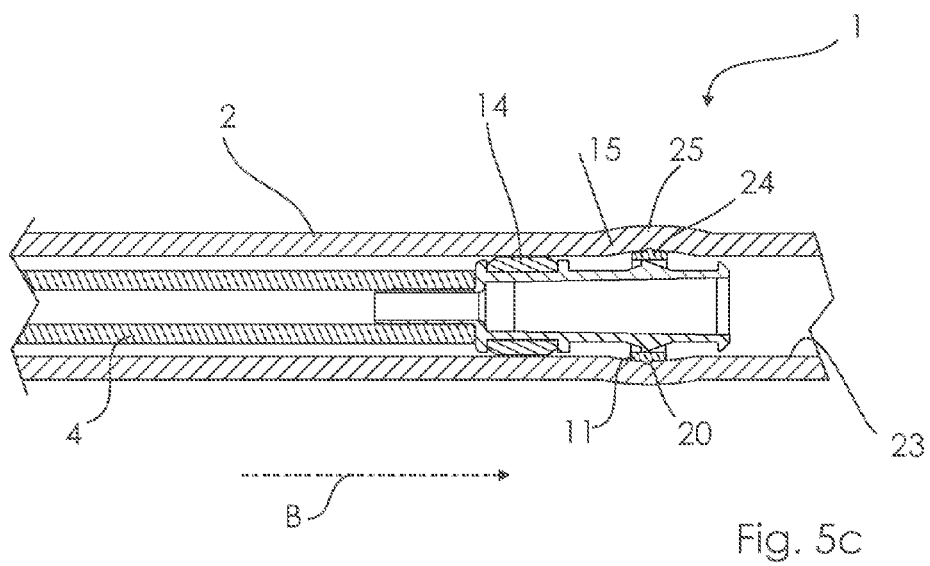
FIG. 5c shows a sectional side view of the same, where the coupling arrangement converts from a first coupling configuration to a second coupling configuration.

However, if enough force, over a predetermined level, is applied to the second telescopic member, the side wall 25 of the first telescopic member will expand as shown in FIG. 5c, allowing the coupling ring to pass the central area 15 of the coupling member 8 and descend towards the first central area. Alternatively, the side wall 25 of the first telescopic member might compress in a radial direction away from the coupling ring obtaining the same effect. Alternatively, if the coupling ring is made of a resilient material, the coupling ring may compress upon the increased force obtaining the same effect. Furthermore, the proximal or distal tapered surface of the coupling member might compress obtaining the same effect. And finally, a combination of the above factors might cause the coupling ring 11 to pass the central area 15 of the coupling member 8 upon the increased application of force to the second telescopic member.

The relationship between the diameter of the inner surface of the first telescopic member, or the outer tube, the diameter of the coupling ring and the diameter of the central area, or the widest part of either the proximal or the distal tapered surface. The outer diameter of the ring $D_R$ may be larger than the inner diameter of the first telescopic member $D_1$: $D_R > D_1$ For the friction between the outer surface of the coupling ring and the inner surface of the outer tube (first telescopic member): $\mu_1 \times FN > \mu_2 \times FN + (\mu_2 \times tg\alpha(FN + F_{ij}))$
FN=Normalforce between the ring and the inside of the tube and the same force is applied between the ring and the tapered surface.; $F_{ij}$=the spring force between the ring and the tapered surface. $\alpha$=the increase in diameter on the tapered surface.

The increasing diameter of the tapered surfaces, either the proximal or the distal surface, is preferably in the ratio between the radius (r) and the height (h): r:h>1:12 and <1:2 (alternative 1:1)

The hardness of the outer tube or the s telescopic member is preferably in the interval Shore 55D-80A for corrugated tubes or tubes with alternating ridges and grooves, while the hardness of a smooth tube is preferably between 50D and 70A.

Figure 6:
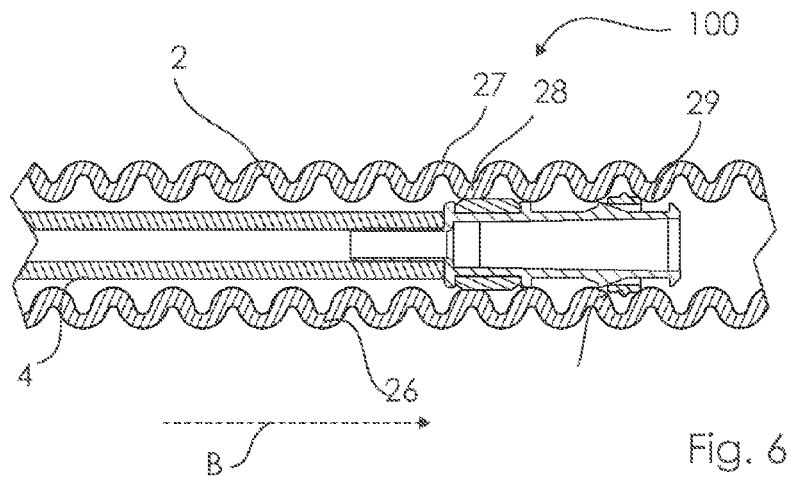
FIG. 6 shows a sectional side view of a telescopic device in accordance with the present invention, where the first telescopic member is a corrugated tubular element.

FIG. 6 shows a telescopic device 100 according to the present invention in a similar configuration as shown in FIG. 5b, where the first telescopic member 2 is a corrugated tubular member 26, having ridges 27 and grooves 28. The coupling ring 11 engages the inner surface 29 of one of the grooves 28, as the outer diameter of the coupling ring 11 is larger than the inner diameter of the inner surface of the grooves 28, causing the increased friction during the movement of the second telescopic member 4 in the direction B and resulting in the same advantages as the embodiment shown in FIG. 5a-c.

The invention claimed is:

1. A telescopic device comprising a first telescopic member and a second telescopic member, where the second telescopic member is displaceably arranged within the first telescopic member so that the second telescopic member can be moved in a first and a second axial direction along the longitudinal axis of the first telescopic member, a coupling arrangement for limiting displacement of the second telescopic member relative to the first telescopic member, the coupling arrangement comprising;
a coupling member having an inner lumen and an external surface, the external surface including a central area, a first tapered surface proximal to the central area tapered to converge in the first axial direction, a second tapered surface distal to the central area tapered to converge in the second axial direction: and
a coupling ring attached to the external surface of the coupling member;
wherein a first coupling configuration of the coupling arrangement limits the displacement of the second telescopic member in the first axial direction and permits displacement of the second telescopic member in the opposite second axial direction.

2. A telescopic device according to claim 1, where the coupling member has a proximal end and a distal end, and where the central area of the external surface of the coupling member has a first outer diameter, the first tapered surface proximal to the central area terminating in a second outer diameter that is smaller than the first outer diameter and the second tapered surface distal to the central area terminating in a third outer diameter that is smaller than the first outer diameter.

3. A telescopic device according to claim 1, wherein the coupling member is attached to a distal end of the second telescopic member.

4. A telescopic device according to claim 1, wherein the coupling ring engages an inner surface of the first telescopic member.

5. A telescopic device according to claim 1, wherein the coupling ring has an outer surface provided with a radial protrusion.

6. A telescopic device according to claim 1, wherein the first proximal tapered surface comprises a stopping means for preventing the coupling ring from maneuvering from the first proximal tapered surface to the central area.

7. A telescopic device according to claim 1, wherein the telescopic device is a urinary catheter.

8. A telescopic device according to claim 1, where a surface of the first and/or the second telescopic member is coated with a hydrophilic coating for provision of a low friction surface.

9. A telescopic device according to claim 1, wherein the telescopic device is packed for storage and/or transport with a liquid swelling medium for wetting the hydrophilic coating and for maintaining the hydrophilic coating in a fully hydrated state during storage and/or transport.

10. A telescopic device according to claim 1, wherein the second telescopic member is a catheter tube having a wall defining an inner lumen, where the wall is provided with drainage eyes and a proximal end having an insertable tip, closing off the inner lumen of the catheter tube.

11. A telescopic device according to claim 1, wherein a length of the first telescopic member is equal to or larger than a length of the second telescopic member.

12. A telescopic device according to claim 1, wherein the first telescopic member is a tubular element having walls of a gas impermeable material.

13. A telescopic device according to claim 1, wherein the telescopic device is provided in a collapsed configuration for storage or transport, where the first telescopic member encloses the second telescopic member and free ends of the first telescopic member are closed by a gas impermeable closure.

14. A telescopic device according to claim 1, wherein the first telescopic member is a corrugated tubular element having a side wall comprising alternating ridges and grooves.

15. A telescopic device according to claim 1, wherein the first telescopic member defines a handle allowing the manipulation of the second telescopic member.

16. A telescopic device according to claim 1, wherein a second coupling configuration of the coupling arrangement limits the displacement of the second telescopic member in the second axial direction and permits displacement of the second telescopic member in the opposite first axial direction.

17. A telescopic device according to claim 1, wherein the coupling ring is a C-shaped coupling ring.

18. A telescopic device including a first telescopic member and a second telescopic member, where the second telescopic member is displaceably arranged within the first telescopic member so that the second telescopic member can be moved in a first and a second axial direction along the longitudinal axis of the first telescopic member, a coupling arrangement for limiting displacement of the second telescopic member relative to the first telescopic member, the coupling arrangement comprising:
   a coupling member having a proximal end and a distal end, and a coupling ring encircling an outer surface of the coupling member, where the outer surface of the coupling member is provided with a central part having a first outer diameter, a first tapered surface proximal to the first central area tapering in the first axial direction and terminating in a second outer diameter that is smaller than the first outer diameter, and a second tapered surface distal to the central area tapering in the second axial direction and terminating in a third outer diameter that is smaller than the first outer diameter.

19. A telescopic device including a first member and a second member, where the second member is telescopibly arranged within the first member so that the second member is configured to move in a first axial direction and in an opposite second axial direction along a longitudinal axis of the first member, and a coupling arrangement configured to limit displacement of the second member relative to the first member, the coupling arrangement comprising:
   a coupling member inserted in the first member and having a proximal end that is inserted in the second member, the outer surface of the coupling member includes a ridge located between a first tapered surface proximal to the ridge and a second tapered surface distal to the ridge; and
   a coupling ring arranged on an outer surface of the coupling member between the ridge and a distal end of the coupling member;
   wherein the coupling ring is configured to translate from the second tapered surface distal to the ridge to the first tapered surface proximal to the ridge and the ridge prevents the coupling ring from translating from the first tapered surface proximal to the ridge to the second tapered surface distal to the ridge.

20. A telescopic device according to claim 19, wherein the telescopic device is a urinary catheter.

21. A telescopic device according to claim 19, wherein the coupling ring is a C-shaped coupling ring.

22. A telescopic device according to claim 19, wherein the ridge in combination with the first member prevents the coupling ring from translating from the first tapered surface proximal to the ridge to the second tapered surface distal to the ridge.

23. A telescopic device according to claim 19, further comprising:
   a seal arranged on the outer surface of the coupling member between the ridge and the proximal end of the coupling member.

24. A telescopic device according to claim 19, wherein the first tapered surface tapers to converge from the ridge to a central longitudinal axis of the coupling member and the second tapered surface tapers to converge from the ridge to the central longitudinal axis of the coupling member.

* * * * *